United States Patent [19]

Borsboom

[11] Patent Number: 4,884,891
[45] Date of Patent: Dec. 5, 1989

[54] FIBRE-OPTIC APPARATUS

[75] Inventor: Petrus C. F. Borsboom, Westeremden, Netherlands

[73] Assignee: Sensoptic Development B.V., Westeremden, Netherlands

[21] Appl. No.: 888,204

[22] Filed: Jul. 23, 1986

[30] Foreign Application Priority Data

Jul. 26, 1985 [NL] Netherlands ......................... 8502138

[51] Int. Cl.$^4$ .......................................... G01N 21/47
[52] U.S. Cl. ............................................... 356/446
[58] Field of Search ............... 356/445, 446, 448, 373, 356/72, 73, 73.1; 250/227; 350/96.15

[56] References Cited

U.S. PATENT DOCUMENTS

| | | | |
|---|---|---|---|
| 3,068,742 | 12/1962 | Hicks et al. | 356/446 X |
| 3,806,256 | 4/1974 | Ishak | 356/446 |
| 4,226,541 | 10/1980 | Tisue | 356/446 |
| 4,310,905 | 1/1982 | Palmer | 367/140 |
| 4,583,858 | 4/1986 | Lebling et al. | 356/446 X |

OTHER PUBLICATIONS

Publication "Fibre Optics Photoelectric Colorimeter", Optica Acta, 1970, vol. 17, No. 10, 725–732.

Primary Examiner—Richard A. Rosenberger
Attorney, Agent, or Firm—Burns, Doane, Swecker & Mathis

[57] ABSTRACT

The invention relates to a fibre-optic apparatus for determining in a material a phenomenon affected by light back-scattered by surface and/or volume refraction. The apparatus comprises a light source; an illuminating system connecting the light source to a sensor head; a light detection system connected to the sensor head; and within the sensor head an optical illuminating fibre connected to the illuminating system, and a juxtaposed optical detection fibre connected to the light detection system. The optical fibres are mounted in a mutually fixed position. In the sensor head according to the invention at least one solid optical illuminating fibre and at least one juxtaposed optical detection fibre are disposed with their optical axes parallel to each other through an axial length from the end of the optical fibres arranged to face the material to be examined, and the optical illuminating fibre is adapted to be also used as an optical detection fibre in addition to the optical detection fibre first mentioned.

4 Claims, 2 Drawing Sheets

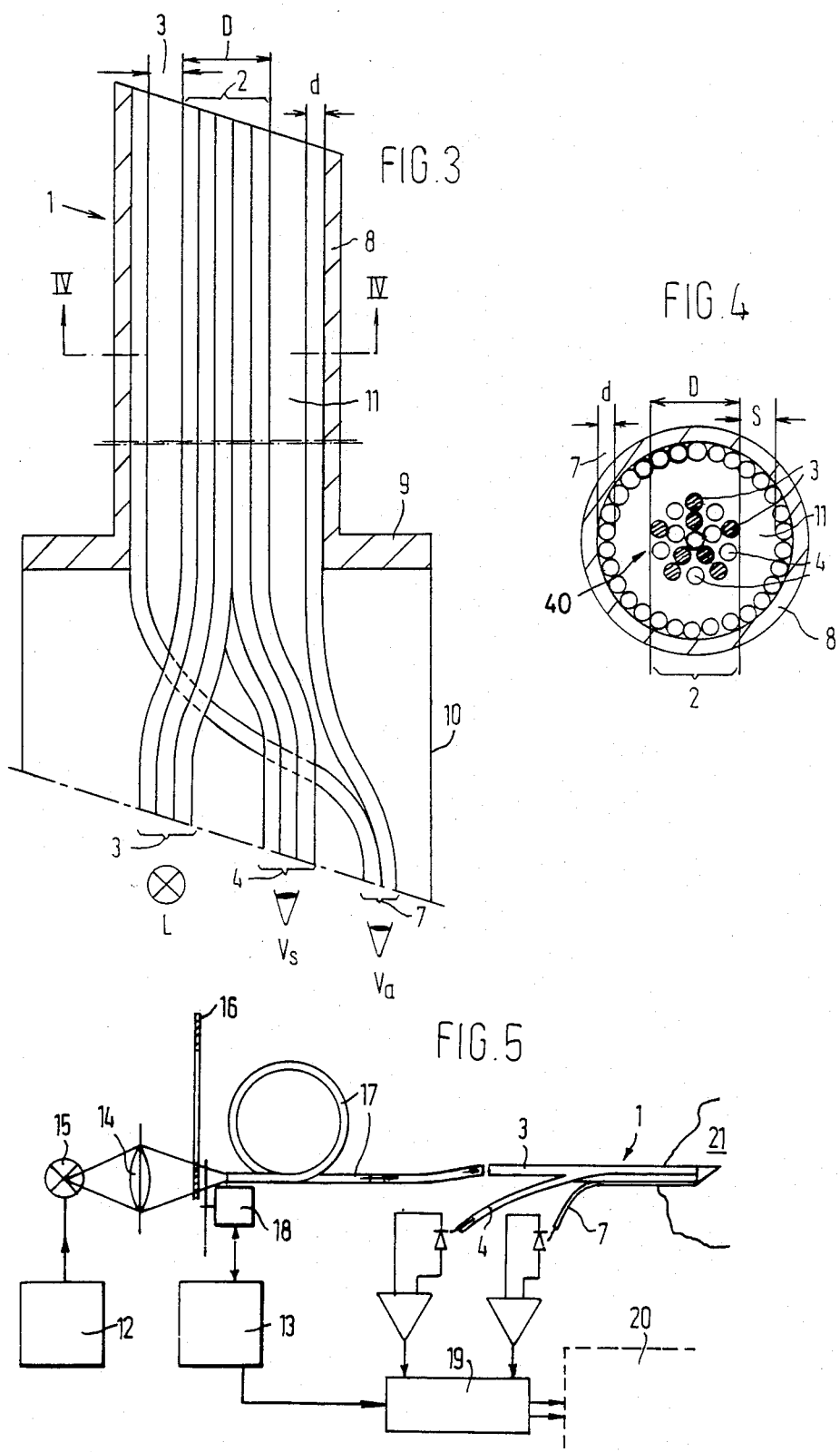

FIBRE-OPTIC APPARATUS

This invention relates to a fibre-optic apparatus for determining in a material a phenomenon affected by light back-scattered by surface and/or volume reflection, comprising a light source; illuminating means connecting the light source to a sensor head; light detection means connected to the sensor head; and within said sensor head an optical illuminating fibre connected to said illuminating means, and a juxtaposed optical detection fibre connected to the light detection means; said optical fibres being mounted in a mutually fixed position.

Designed as a photoelectric colorimeter, and suitable for use as an apparatus for automatic colour control in the preparation of paint, an apparatus as defined above is known from the article by I. G. H. Ishak "Fibre optics photoelectric colorimeter", Optica Acta, 1970, Volume 17, No. 10, pp 725-732. As in all photoelectric colorimeters, Ishak's measuring principle is also based on the duplication, by physical means using colour filters, of the so-called C.M.F. (Colour Matching Functions) $x_\lambda$, $y_\lambda$, and $z_\lambda$, being the three spectral sensitivity functions defining the characteristics of the eye of a standard observer, fitting the system of the specification of colours designed by the Commision Internationale de l'Eclairage (C.I.E.).

Within the framework of the fibre-optic photoelectric colorimeter developed by him, Ishak uses a sensor head in which the geometry of illuminating and receiving the reflected light is 0°/45°. For this purpose, the sensor head, which is of hemispherical configuration, is provided with 7 holes with radial axes. One of the holes is formed in the top of the hemispherical sensor head, and is optically coupled, as an illuminating element, via an optical fibre, to a light source, the other 6 holes being equidistantly and symmetrically spaced along the circumference of the hemispherical sensor head at angles of 45°, and being connected through 6 optical fibres to the detector. The light reflected by the material being investigated is thus collected at an angle of 45° from six different directions by the corresponding optical fibres. In the colorimeter proposed by Ishak, therefore, it is of great importance that the reflection of the material being investigated is isotropic.

Paint, for which material Ishak has developed his fibre optic colorimeter, is an example of an opaque material. Opaque materials are distinguished by a high absorption and scattering coefficient with values $>>10$ $mm^{-1}$, and hence have very slight light penetration depths. CIE-calibrated reflectometers as the Ishak colorimeter are intended for use with opaque materials. When such meters are used for translucent materials, which are characterized by relatively low absorption and scattering coefficients with values of 10 $mm^{-1}$–0,01 $mm^{-1}$ (with the absorption coefficient $<<$ the scattering coefficient), however, measuring problems are encountered, caused by so-called peripheral leakage. By this is understood the effect that a narrow light beam incident upon a translucent material is widened as a result of volume scattering and reflection in the reverse direction in the translucent material. This widening manifests itself as a broad light spot around the beam incident upon the translucent material according to the normal. In addition, the light volume-scattered in the translucent material can be absorbed during its passage through the translucent material. This absorption depends on the concentration of the absorbing material. The effect of the absorbing material manifests itself in a change of the light intensity distribution of the light spot. The light absorption results in colour influencing.

The light back-scattered in the centre and within the diameter of the illuminating beam, which hence has traversed a short path in the translucent material, is mainly determined by the scattering characteristics of the material only.

Examples of translucent materials are: virtually all biological materials, such as muscle tissue, skin, milk, cheese, fruit. Furthermore, milk-like liquids, dispersions of powdered materials in liquid, and paper are other examples of translucent materials.

In addition to paint, examples of opaque materials are metals or their oxides.

It is an object of the present invention, within the frame work of the above, to provide apparatus of the kind defined in the opening paragraph hereof, and which is more generally applicable, that is to say, can be used for both translucent and opaque materials for optically determining a phenomenon that is affected by surface and/or volume reflection of light, for example, the colour and/or brightness of the material.

For this purpose the apparatus according to the invention is characterized in that in said sensor head, at least one solid optical illuminating fibre and at least one juxtaposed optical detection fibre are disposed with their optical axes parallel to each other through an axial length from the end of the optical fibres arranged to face the material to be examined, said optical illuminating fibre being adapted to be also used as an optical detection fibre in addition to the optical detection fibre.

In the apparatus according to the invention the light which the material being investigated back-scatters when illuminated with a light beam is collected and measured at two spaced areas. The back-scattered light collected by the illuminating fibre will have covered a short path in the material being investigated, and be hardly, if at all, absorbed. The back-scattered light collected in the juxtaposed detection fibre has traversed a longer path through the material, and will have been partly absorbed in the presence of absorbing substances in the translucent material. It has been found that the colour of the material being investigated is the result of the (back)scattering and absorption processes together.

In the apparatus according to the invention, the illuminating fibre may be connected to a first part of the light detection means, comprising means for measuring light back-scattered by the material being investigated and entering within the angle of acceptance of the optical illuminating fibre. Specifically, the sensor head may mount a single solid optical illuminating fibre having a diameter of D and one or more juxtaposed optical detection fibres with a diameter d, with D>d, spaced apart a radial distance s, measured between the walls of the optical illuminating fibre and the juxtaposed optical detection fibre or fibres, with the juxtaposed optical detection fibre or fibres being connected to a second part of the light detection means, comprising means for measuring light back-scattered by the material being investigated and entering at a radial distance from the wall of the optical illuminating fibre within the angle of acceptance of the juxtaposed optical detection fibre or fibres. A large variety of materials can be measured in practice if, in accordance with another preferred embodiment of the invention, the diameter D is approximately equal to or larger than four times the inverse of the scattering coefficient of the material to be investigated, the radial distance s is in the order of twice the inverse of the scattering coefficient with an absorption coefficient of the material to be investigated that is equal to, or less than the scattering coefficient, but not less than about 0.1 time the scattering coefficient, and d is about 1/5 of the radial distance s. The terms 'scattering coefficient' and 'absorption coefficient' are well-known in the optical art and defined in the laws of Kubelka-Munk and Lambert-Behr, respectively.

In one embodiment of the apparatus according to the invention the optical illuminating fibre is branched into a first branch forming the connection with the illuminating means, and a second branch connected to the first part of the light detection means.

The light which serves to illuminate the material being investigated is then, coming from the light source, passed into one of the short branches of the Y-shaped illuminating fibre. At the side of the measuring tip of the sensor head (the long branch of the Y-shaped branched illuminating fibre) this light will exit at an exit angle determined by the index of refraction of the material of the optical fibre or the index of refraction of the envelope.

The reflected light entering at the measuring tip end of the illuminating fibre, coming from the material being investigated as a result of surface and volume reflection, is determined by the so-called angle of acceptance of the illuminating fibre, which is equal to the exit angle $\alpha$. The light thus entering is detected at the other of the short branches of the Y-shaped branched illuminating fibre. For proper conduction of the light in the illuminating fibre, care is taken that the angle between each of the short branches of the Y-shaped central optical fibre and the optical axis of the long branch of this fibre is no larger than half the emergent angle $\alpha$.

In practice it may be recommendable to provide a film between the measuring tip and the material being investigated of a medium having an index of reflection less than that of the optical fibre.

The position of the light conductors in the sensor head, that is to say, of the illuminating fibre and of the parallel, juxtaposed detecting fibre(s) is fixed. In a further elaboration of the apparatus according to the invention, the fixation system and the light conductors are housed within a tube, preferably of stainless steel.

At the front or measuring tip side, this (measuring) tube can be bevelled with the angle of bevel $\beta$ to the optical axis being less than the total-reflection angle of the optical fibres. In practice, $\beta$ is generally about 65°. Owing to this construction of the measuring tube it can be inserted into a material being investigated that lends itself thereto, so that the apparatus according to the invention is suitable for use as an invasive meter for the performance of what could be called three-dimensional assays.

The position of the optical fibres within the sensor head relative to each other that is optimal for absorption depends on the nature of the material to be investigated and, if desired, is determined by experimentation. For this purpose a sensor head could be made in which a large number of juxtaposed optical fibres of diameter d is arranged concentrically around a central optical fibre with an increasing radius. Measurements made with such a sensor head give a good picture of the amount of reflected light that has entered the fibres arranged concentrically in rings, and hence of the light reflection as a function of the distance from the light beamed into the material being investigated, in other words, of the optimum optical construction.

The invention will be described and explained in more detail hereinafter with reference to some embodiments of the sensor head associated with the apparatus according to the invention, which are illustrated, by way of example, in the accompanying drawings. In said drawings, FIG. 1 is an axial sectional view of a sensor head according to the present invention, which includes a central optical illuminating fibre and a plurality of juxtaposed optical detection fibres equidistantly spaced therefrom;

FIG. 3 is an axial sectional view, illustrating a different embodiment of a sensor head belonging to an apparatus according to the present invention;

FIG. 4 is a radial sectional view, taken on the line IV—IV of FIG. 3; and

Figure 1:
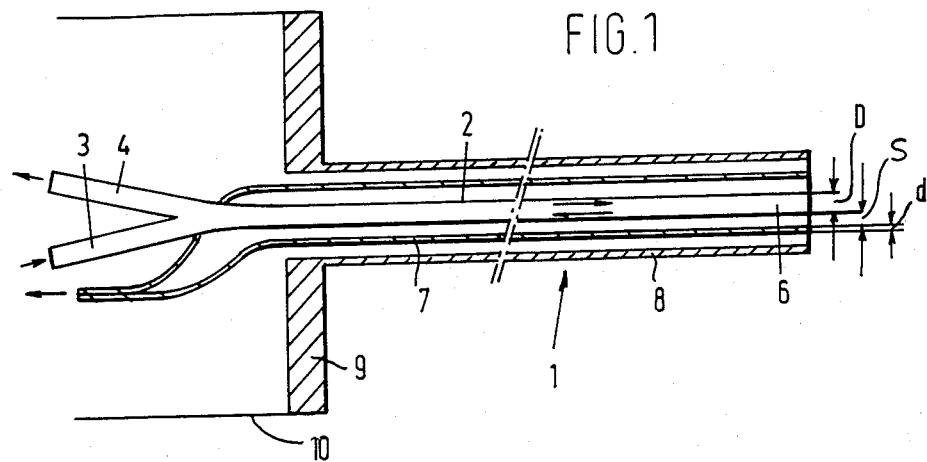

FIG. 5 diagrammatically shows an apparatus according to the present invention.

In the accompanying FIGS. 1–5, like reference numerals designate parts having analogous functions.

Referring to the drawings, there is shown a sensor head 1.

Designated by 2 is a central solid optical fibre with diameter D, which is branched in the shape of a Y to exhibit two short branches 3 and 4 and, at the (non-bevelled) measuring tip side 5 of sensor head 1, the long branch 6.

Arranged in a ring around, and coaxially with, the central fibre 2 are four juxtaposed optical fibres 7. The entire system of optical fibres is fixed, in a manner not shown, within a tube 8 of stainless steel. The tube has a flange 9, with which it is connected to a housing 10, within which the part of the central fibre with branches 3 and 4 and the bundled four juxtaposed optical fibres 7 are arranged.

The branch 3 of the central optical fibre 2 is connected through the light conducting system not shown to a source of light, and branch 4 is connected via the light detection system not shown to a detector for the reflected light which, coming from the material being investigated, along with scattered light from the central fibre itself, has entered at the measuring tip end of the long branch 6 of the central optical fibre.

As a source of light 15 (FIG. 5), use can be made of a halogen lamp of 50 W, 12 V and with a filament temperature of about 3000 K. The lamp is supplied with electricity from a stable source of voltage 12 of $\Delta V = 5.10^{-4}$ at 12 V D.C. as an alternative for the source of light, use can be made of a so-called LED (Light Emitting Diode), current and temperature stabilized with an A.C. source of about 1000 Hz. In this arrangement the wavelength spectrum of the LED will have to be adapted to the absorption characteristics of the translucent material to be investigated. Other types of light sources, provided they have a stabilized light output, are also suitable. In the case of a D.C. fed light source, the luminous flux is pulsed by means of a chopper wheel 18 driven by a synchronous motor to be rotated at such a rate that the luminous flux is interrupted at a frequency of about 1000 Hz.

The light from the light source is subsequently focussed via a condenser lens 14 onto the input of a flexible optical fibre as a light conductor 17 forming part of the light conducting system, and transported further via the light conducter to branch 13 of the central fibre 2 in the sensor head.

In front of the input of the flexible light conductor, a monochromator or a colour or interference filter 16 can be placed, depending on the use of the apparatus or on the absorption characteristics of the material to be investigated, for example, translucent material. Thus, in the case of measurements with regard to meat, for which the apparatus according to the invention is very suitable, an interference filter is used with a transmission at 560 nm, corresponding to the absorption by haemoglobin and myoglobin, which occur in the meat.

For the further processing of the back-scattered light which, coming from the material being investigated, has entered the central optical fibre 2 and has been conducted into branch 4, or has entered the juxtaposed optical fibres 7, branch 4 and the juxtaposed fibres 7 are each coupled via an intensifying system to a detector. The signal from the detector coupled to branch 4 of the central optical fibre, is supplied to the measuring side of a twin-channel synchronous detector 19, as is the signal from the detector coupled to the parallel juxtaposed fibres 7, and the measuring results are further processed in section 20 of the apparatus and recorded in a suitable and desired manner.

If the apparatus according to the invention, with the sensor shown in the drawing, is used for examination regarding a material whose scattering coefficient is high relative to the inverse of the diameter D of the central fibre at the measuring side of the sensor head, the parallel juxtaposed fibres 7 will receive no reflected light. Thus in the case of opaque materials, such as paint, in which the light leakage effect (peripheral leakage effect) no longer plays a role at a diameter D of 5 mm, the apparatus will function as a true reflectometer. This means that, apart from the measuring geometry of the sensor head, the apparatus according to the invention is comparable to the standard CIE colorimeter. The apparatus could in this case be used, for example, as an invasive paint colorimeter for wavelength-dependent measurements, in which the central optical fibre 2 is used only.

Before being used in practice, a sensor head will have to be calibrated, for which the procedure, for a given translucent material, is as follows. The measuring tip side of the sensor head is immersed in a clear liquid contained in a beaker which is dull black on the inside, well spaced from the beaker bottom. The index of refraction of the liquid must be known (for example, water). A white insoluble powdered solid is added to the liquid, whose particle size or particle size distribution is known (e.g., Latex of particle size $\approx 1 /\mu m$).

In this way three solutions are prepared, for example, such that the first solution gives a deflection of 30% relative to the deflection of the translucent material to be measured; the second solution the same deflection, and the third solution twice (200%) the deflection of the translucent material to be measured (deflection of the signal from the central fibre). Of these three solutions, four subdivisions are made: 1, 1a, 1b, 1c; 2, 2a, 2b, 2c and 3, 3a, 3b and 3c.

Subsequently, a colour is added to the solutions in such a quantity that, in the case of the "a" solutions, the deflection of the detector at the parallel juxtaposed fibres is 30% of the value of the deflection of the translucent material; in the case of the "b" solutions equal to that value; and in the case of the "c" solutions 200% of that value.

A suitable colour is a substance which exhibits a corresponding absorption spectrum to that of the translucent material. Both the added concentration of the white powder and of the colour should be determined. After the solutions have been obtained, the linear scattering and absorption coefficients can be determined by the dilution method as used as a standard procedure in chemical analyses and using a spectrophotometer (Lambert-Beer method).

It is true that, for one thing owing to its structure, the translucent material will differ in scattering and absorption behaviour relatively to the calibrating liquid, but the advantage is that the liquid composition and the assays are reproducible. Furthermore, it is often not feasible to find a substance that is similar in structure. Thus a measuring head with a fixed configuration needs to be calibrated only once for each application. For the daily check of the measuring head and other elements, a simple translucent material, for example, a plastic strip, can be used, which has been calibrated relatively to the above calibrating liquids.

The most important use of the colorimeter will probably be in the field of biological materials. As these biological materials cover a limited range for the scattering and absorption coefficient thereof, the sensor head can be based on a fixed configuration, that is to say, a central optical fibre with diameter D=2 mm; a distance s of about 1 mm; a thickness d of the juxtaposed optical fibre of about 0.25 mm; an angle of acceptance of about 15°–20°; an exterior diameter of the housing of stainless steel of 7 mm with a bevel of an angle $\beta$ of about 65°. Using a fibre-optical apparatus according to the invention, provided with such a sensor head, assays have been made with regard to freshly-slaughtered veal and veal 48 hours old in a production-line export slaughterhouse.

As will be clear, the colour of slaughtered meat is an important quality standard. In the slaughterhouse, colour is assayed on the basis of visual perception, using a colour scale composed by a number of colour inspectors, also on the basis of visual perception. The colour scale comprises meat colour gradations in eight groups 1–8. Group 1 represents lightly-coloured meat of the highest quality and group 8 the darkest-coloured meat, corresponding to the least quality. The intermediate groups represent a regular transition from light to dark colours and of decreasing quality in the direction of group 1 to group 8.

Colour measurements were made with samples of fresh meat and meat 48 hours old in the form of slices of meat all cut from analogous places of the corresponding carcasses.

The colour assays were made both visually in the usual manner, using the colour scale with colour groups 1–8, and with the apparatus according to the present invention with the above-described sensor head.

Figure 2:
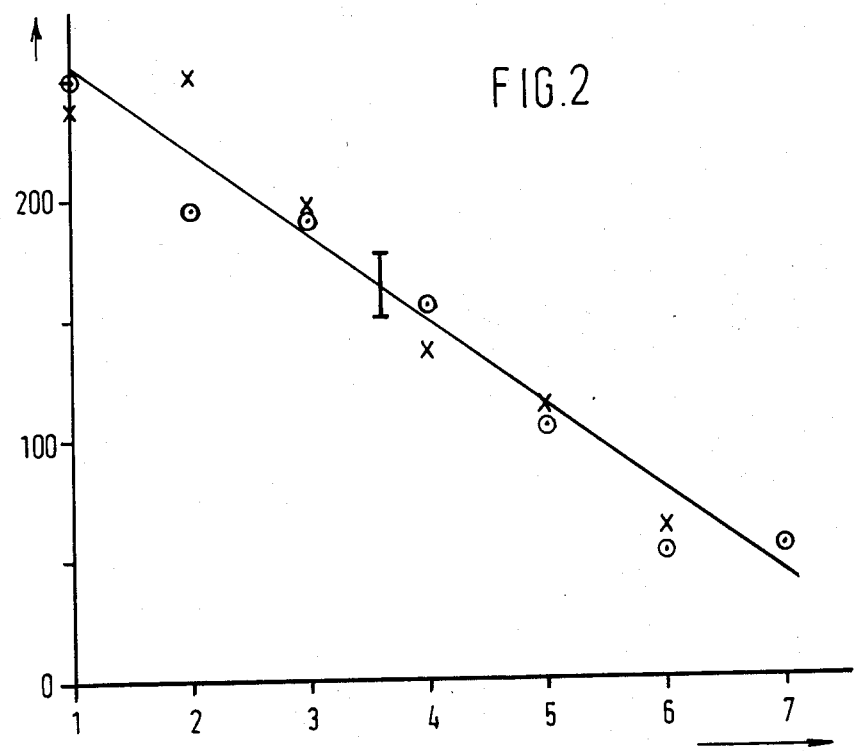
FIG. 2 shows graphically the result of comparative measurements, made on veal, using an apparatus with a sensor head as illustrated in FIG. 1 and visually in the conventional manner.

The results of these measurements are shown graphically in the accompanying diagram of FIG. 2, in which the signal relevant for the absorption, measured with the sensor head via the juxtaposed optical fibre is plotted in mV along the vertical axis, and the visual colour scale with colour groups 1–8 along the horizontal axis.

The points indicated by crosses concern the measurements of slices of fresh meat and the circled points slices of meat 48 hours old.

The diagram clearly shows the relationship between the colour scale for visual perception and the absorption signal measured with the sensor head.

As was to be expected, measurements via the central fibre of the sensor head did not provide any essential colour information, but did provide information relevant to scattering and brightness, caused by the structure of the meat, for example, the structure of muscle bundles, fat, etc. Scattering measurement is of importance in meat quality assay as providing an insight into possibly deviant and less desirable meat structures, and in this way safe limit conditions are given within which relevant absorption measurements can be made.

I claim:

1. A fibre-optic apparatus for determining in a material to be examined a phenomenon affected by light back-scattered by surface and/or volume reflection, the material being described by a scattering coefficient and the apparatus comprising a light source; illuminating means connecting the light source to a sensor head; light detection means connected to the sensor head; and within said sensor head an optical illuminating fibre connected to said illuminating means, and a juxtaposed optical detection fibre connected to the light detection means; said optical fibres being mounted in a mutually fixed position, characterized in that, in said sensor head (1), at least one solid optical illuminating fibre (2) and at least one juxtaposed optical detection fibre (7) are disposed with their optical axes parallel to each other through an axial length from the end of the optical fibres arranged to face the material to be examined, said optical illuminating fibre (2) being adapted to be also used as an optical detection fibre in addition to the optical detection fibre (7), said optical illuminating fibre (2) having a diameter D and being connected to a first light detection means comprising means for measuring light back-scattering from the material (21) being examined and entering within an angle of acceptance of the optical illuminating fibre (2), said at least one juxtaposed optical detection fibre (7) having a diameter d, with $D \geq d$, being spaced apart a radial distance S measured between the walls of the optical illuminating fibre (2) and the at least one juxtaposed optical detection fibre (7), and said at least one juxtaposed optical detection fibre (7) being connected to a second light detection means comprising means for measuring light back-scattering from the material (21) being examined and entering at the radial distance S from the wall of the optical illuminating fibre within an angle of acceptance of the at least one juxtaposed optical detection fibre (7), with d being about 1/5 of the radial distance S.

2. Apparatus as claimed in claim 1, characterized in that the optical lluminating fibre (2) is connected to a first part of the light detection means and the at least one juxtaposed fibre (7) is connected to a second part of the light detection means.

3. Apparatus as claimed in claim 1, characterized in that the optical illuminating fibre (2) is branched into a first branch (3) forming the connection to the illuminating means, and a second branch (4) connected to the light detection means.

4. Apparatus as claimed in claim 1, characterized in that the sensor head (1) comprises a rigid tube (8) with an interior radius R, the hollow interior of which is packed with an array of optical fibres of substantially equal diameters, to a degree of packing at which the optical fibres are substantially immovable in said tube in the radial direction, and within which array a marginal group and a core group (40) of the optical fibres are selected, the core group (40) having a diameter D about the axis of the rigid tube (8), of which core group (40) in a random pattern a number of the optical fibres are singled out and, with their ends (3), via the connection to the illuminating means, formed to the optical illuminating fibres, and the remainder of the optical fibres from said core group (40) being singled out and having their ends (4) connected to a first part of the light detection means, the individual optical fibres from the marginal group of fibres being contiguous with the inner wall of tube (8) and having their ends (7) connected to a second part of the light detection system, the diameter of the optical fibres in tube (8) being d, and the radial distance between the circumference of the core group (40) and the inner circumference of the marginal group of optical fibres contiguous with the inner wall of tube (8) being S, wherein d is about 1/5 of S.

* * * * *